United States Patent
Joseph

(10) Patent No.: US 9,687,295 B2
(45) Date of Patent: Jun. 27, 2017

(54) METHODS OF MANUFACTURING A PAIR OF JAW MEMBERS OF AN END-EFFECTOR ASSEMBLY FOR A SURGICAL INSTRUMENT

(71) Applicant: COVIDIEN LP, Mansfield, MA (US)

(72) Inventor: Daniel A. Joseph, Golden, CO (US)

(73) Assignee: COVIDIEN LP, Mansfield, MA (US)

( * ) Notice: Subject to any disclaimer, the term of this patent is extended or adjusted under 35 U.S.C. 154(b) by 254 days.

(21) Appl. No.: 14/564,325

(22) Filed: Dec. 9, 2014

(65) Prior Publication Data
US 2015/0297288 A1 Oct. 22, 2015

Related U.S. Application Data

(60) Provisional application No. 61/980,742, filed on Apr. 17, 2014.

(51) Int. Cl.
| | | |
|---|---|---|
| *B21D 39/03* | (2006.01) | |
| *B23P 11/00* | (2006.01) | |
| *A61B 18/14* | (2006.01) | |
| *A61B 17/00* | (2006.01) | |

(52) U.S. Cl.
CPC ...... *A61B 18/1445* (2013.01); *A61B 2017/00526* (2013.01); *A61B 2018/1455* (2013.01); *Y10T 29/49826* (2015.01); *Y10T 29/49895* (2015.01)

(58) Field of Classification Search
CPC ......... Y10T 29/49208; Y10T 29/49826; Y10T 29/49895; Y10T 279/1986; Y10T 29/53887; B25B 7/02
USPC .................. 29/428, 464, 469, 527.1, 854
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 14/098,953, filed Dec. 6, 2013; inventor: Cunningham.

(Continued)

*Primary Examiner* — Thiem Phan

(57) ABSTRACT

A method of manufacturing a matched pair of opposing jaw members of an end-effector assembly includes assembling a first jaw member having a knife channel, assembling a second jaw member having a knife channel, setting a jaw gap and aligning a first sealing plate of the first jaw member and a second sealing plate of the second jaw member in relation to one another by bringing the first jaw member and the second jaw member into clamped engagement with an alignment spacer. The alignment spacer is configured to engage the knife channel of the first jaw member and the knife channel of the second jaw member. The method also includes coupling the first jaw member to the second jaw member.

19 Claims, 9 Drawing Sheets

(56) References Cited

U.S. PATENT DOCUMENTS

| | | |
|---|---|---|
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,425,743 A | 6/1995 | Nicholas |
| 5,527,313 A | 6/1996 | Scott et al. |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,197,633 B2 | 6/2012 | Guerra |
| 8,267,935 B2 | 9/2012 | Couture et al. |
| D670,808 S | 11/2012 | Moua et al. |
| D680,220 S | 4/2013 | Rachlin |
| 8,491,626 B2 | 7/2013 | Roy et al. |
| 2007/0074807 A1 | 4/2007 | Guerra |
| 2011/0190765 A1 | 8/2011 | Chojin |
| 2013/0345701 A1 | 12/2013 | Allen, IV et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 2006/021269 A1 | 3/2006 |

(56) References Cited

FOREIGN PATENT DOCUMENTS

| WO | 05110264 A3 | 4/2006 |
|---|---|---|
| WO | 2008/040483 A1 | 4/2008 |
| WO | 2011/018154 A1 | 2/2011 |

OTHER PUBLICATIONS

U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999. (1 page).
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447. cited by applicant.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).

Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831. cited by applicant.
Sampayan et al, "Multilayer Ultra-High Gradient Insulator Technology" Discharges and Electrical Insulation in Vacuum, 1998. Netherlands Aug. 17-21, 1998; vol. 2, pp. 740-743. cited by applicant.
Paul G. Horgan, "A Novel Technique for Parenchymal Division During Hepatectomy" The American Journal of Surgery, vol. 181, No. 3, Apr. 2001 pp. 236-237. cited by applicant.
Benaron et al., "Optical Time-Of-Flight and Absorbance Imaging of Biologic Media", Science, American Association for the Advancement of Science, Washington, DC, vol. 259, Mar. 5, 1993, pp. 1463-1466. cited by applicant.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157. cited by applicant.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/ Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Sayfan et al. "Sutureless Closed Hemorrhoidectomy: A New Technique" Annals of Surgery vol. 234 No. 1 Jul. 2001; pp. 21-24. cited by applicant.
Levy et al., "Update on Hysterectomy—New Technologies and Techniques" OBG Management, Feb. 2003. (15 pages.).
Dulemba et al. "Use of a Bipolar Electrothermal Vessel Sealer in Laparoscopically Assisted Vaginal Hysterectomy" Sales/Product Literature; Jan. 2004. (1 page).

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574. cited by applicant.
Sengupta et al., "Use of a Computer-Controlled Bipolar Diathermy System in Radical Prostatectomies and Other Open Urological Surgery" ANZ Journal of Surgery (2001) 71.9 pp. 538-540. cited by applicant.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17. cited by applicant.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005. cited by applicant.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.
U.S. Appl. No. 14/065,644, filed Oct. 29, 2013; inventor: Reschke.

METHODS OF MANUFACTURING A PAIR OF JAW MEMBERS OF AN END-EFFECTOR ASSEMBLY FOR A SURGICAL INSTRUMENT

CROSS REFERENCE TO RELATED APPLICATION

The present application claims the benefit of and priority to U.S. Provisional Application Ser. No. 61/980,742, filed on Apr. 17, 2014, the entire contents of which are incorporated herein by reference.

BACKGROUND

1. Technical Field

The present disclosure relates to surgical instruments. More particularly, the present disclosure relates to end-effector assemblies for use in surgical instruments and methods of manufacturing a pair of jaw members of an end-effector assembly.

2. Discussion of Related Art

Bipolar electrosurgical forceps have an end-effector assembly with electrodes on the inner, opposing surfaces of pivotally movable jaw members. The electrodes are electrically coupled to an electrosurgical generator, with the electrode on one jaw member actively delivering electrosurgical energy and the electrode on the other jaw member functioning as a return, thereby creating an electrical circuit through tissue grasped by the jaw members.

Tissue grasped by the jaw members can be treated to different degrees (e.g., cauterized, coagulated, desiccated or sealed) depending on the intensity, frequency and duration of the electrosurgical energy applied by the electrodes. The effectiveness of the electrosurgical energy on the tissue is affected by mechanical factors such as the pressure applied to the tissue when grasped by the jaw members and the gap distance between the electrodes.

Predictability in such mechanical factors can be provided by meeting specific tolerance requirements when manufacturing the end-effector assembly of the electrosurgical forceps. It would be desirable to develop manufacturing methods for end-effector assemblies to meet tolerance requirements such as gap tolerances, alignment of the jaw members and the like.

SUMMARY

End-effector assemblies that meet design tolerance requirements are provided by the manufacturing processes described herein.

According to an aspect of the present disclosure, a method of manufacturing a pair of opposing jaw members of an end-effector assembly includes assembling a first jaw member having a knife channel, assembling a second jaw member having a knife channel, setting a jaw gap and aligning a first sealing plate of the first jaw member and a second sealing plate of the second jaw member in relation to one another by bringing the first jaw member and the second jaw member into a clamped engagement with an alignment spacer. The alignment spacer is configured to engage the knife channel of the first jaw member and the knife channel of the second jaw member. The method also includes coupling the first jaw member to the second jaw member.

According to another aspect of the present disclosure, a method of manufacturing a pair of opposing jaw members of an end-effector assembly is provided. The method includes the initial steps of assembling a first jaw member, including: coupling an electrical lead to a first sealing plate; overmolding a first insulator member onto the first sealing plate; and coupling a first support structure to the first insulator member; and assembling a second jaw member, including: overmolding a second insulator member onto a second sealing plate; and coupling a second support structure to the second insulator member. The method also includes setting a jaw gap and aligning the first sealing plate and the second sealing plate in relation to one another by bringing the first jaw member and the second jaw member into clamped engagement with an alignment spacer configured to engage a first knife channel defined by the first insulator member and a second knife channel defined by the second insulator member; and movably coupling the first jaw member to the second jaw member while in clamped engagement with the alignment spacer.

In any one of the preceding aspects, the alignment spacer may be configured to set a tip bias of the first jaw member and the second jaw member.

In any one of the preceding aspects, the method also includes releasing the alignment spacer from the pair of opposing jaw members.

BRIEF DESCRIPTION OF THE DRAWINGS

Objects and features of the end-effector assemblies for use in surgical instruments and methods of manufacturing a pair of jaw members of an end-effector assembly of the present disclosure will become apparent to those of ordinary skill in the art when descriptions of various embodiments thereof are read with reference to the accompanying drawings, of which.

DETAILED DESCRIPTION

Figure 1:
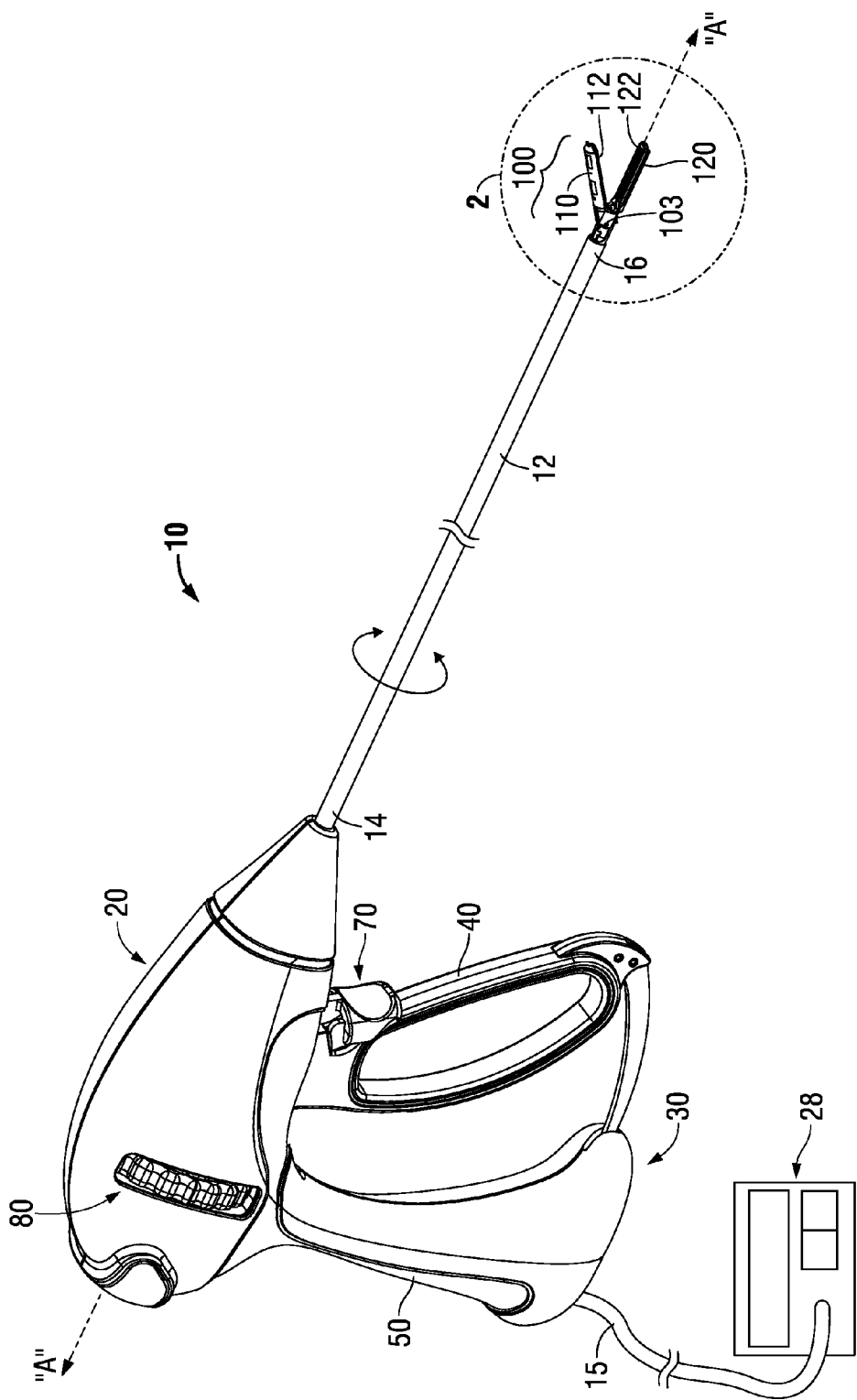
FIG. 1 is a perspective view of a surgical instrument in accordance with an embodiment of the present disclosure.

Hereinafter, embodiments of end-effector assemblies for use in surgical instruments and methods of manufacturing a pair of jaw members of an end-effector assembly of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide surgical instruments, e.g., surgical forceps, suitable for sealing, cauterizing, coagulating/desiccating and/or cutting vessels and vascular tissue. Embodiments of the presently-disclosed surgical instruments may be suitable for utilization in endoscopic surgical procedures and/or suitable for utilization in open surgical applications.

Various embodiments of the present disclosure provide end-effector assemblies for use in surgical instruments. Embodiments of the presently-disclosed end-effector assemblies include a pair of opposing jaw members. One or more of the jaw members include a support structure, an electrical lead, and a sealing plate coupled to the electrical lead. Embodiments of the presently-disclosed jaw members include an insulator member disposed between the support structure and the sealing plate.

Various embodiments of the present disclosure provide methods of manufacturing a matched pair of jaw members of an end-effector assembly. Embodiments of the presently-disclosed methods of manufacturing a matched pair of jaw members include setting a jaw gap and aligning the sealing plates in relation to one another.

Various embodiments of the present disclosure provide an alignment spacer for use in connection with the manufacture of a matched pair of jaw members. Embodiments of the presently-disclosed alignment spacers are configured to align the sealing plates in relation to one another and also configured to set jaw gap and/or to set the tip bias of the jaw members.

In FIG. 1, a surgical instrument generally identified as forceps 10 is shown for use in connection with endoscopic surgical procedures and includes a housing 20, a handle assembly 30, a rotatable assembly 80, a trigger assembly 70, and an end-effector assembly 100 including a pair of jaw members 110 and 120. In one embodiment, the jaw members 110 and 120 may be a matched pair. Forceps 10 may include additional, fewer, or different components than shown in FIG. 1, depending upon a particular purpose or to achieve a desired result. Forceps 10 generally includes an elongated shaft 12 that defines a longitudinal axis "A-A", and supports the end-effector assembly 100. Shaft 12 defines a central lumen therethrough to facilitate translational movement of other components, e.g., to impart movement to the jaw members 110 and 120. One or more components of the forceps 10, e.g., the housing 20, the rotatable assembly 80, the handle assembly 30, the trigger assembly 70, and/or the end-effector assembly 100, may be adapted to mutually cooperate to grasp, seal and/or divide tissue, e.g., tubular vessels and vascular tissue.

Figure 2:
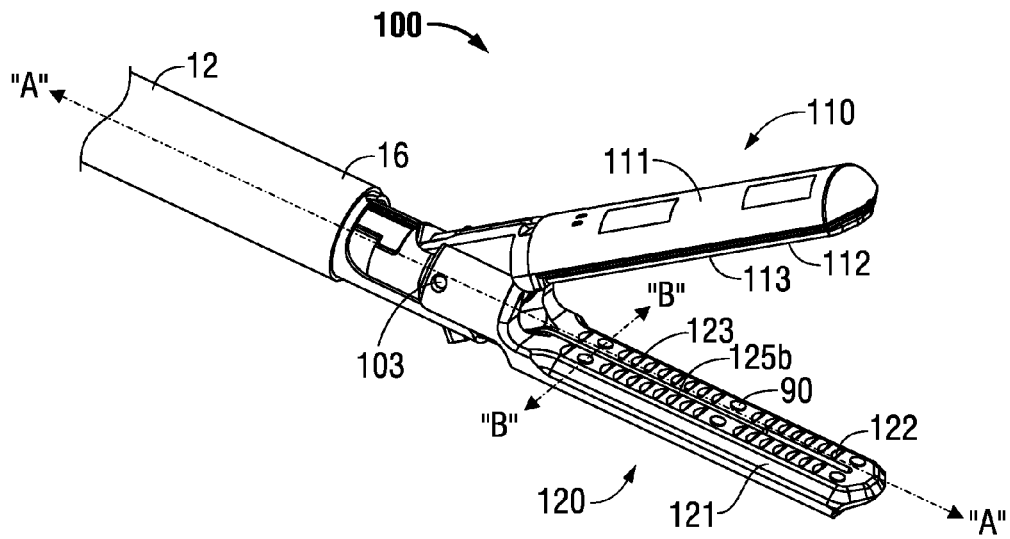
FIG. 2 is a perspective view of the indicated area of detail of FIG. 1.

As depicted in FIG. 1, the end-effector assembly 100 is rotatable in either direction about the longitudinal axis "A-A" through rotation, either manually or otherwise, of the rotatable assembly 80. A transverse axis "B-B" is shown in FIG. 2. The transverse axis "B-B" is perpendicular or substantially perpendicular to the longitudinal axis "A-A". End-effector assembly 100 may include any feature or combination of features of the jaw member embodiments disclosed herein.

End-effector assembly 100 may be configured as a bilateral jaw assembly, i.e., both jaw members 110 and 120 move relative to one another. Alternatively, the forceps 10 may include a unilateral assembly, i.e., the end-effector assembly 100 may include a stationary jaw member, e.g., jaw member 120, mounted in fixed relation to the shaft 12 and a pivoting jaw member, e.g., jaw member 110, mounted about a pivot pin 103 coupled to the stationary jaw member. Jaw members 110 and 120 may be curved at various angles to facilitate manipulation of tissue and/or to provide enhanced line-of-sight for accessing targeted tissues.

As shown in FIG. 1, the shaft 12 has a distal end 16 configured to mechanically engage the end-effector assembly 100. The proximal end 14 of the shaft 12 is received within the housing 20 or is otherwise engaged to the housing 20, and connections relating thereto are disclosed in commonly-assigned U.S. Pat. No. 7,156,846 entitled "Vessel Sealer And Divider For Use With Small Trocars And Cannulas," commonly-assigned U.S. Pat. No. 7,597,693 entitled "Vessel Sealer And Divider For Use With Small Trocars And Cannulas" and commonly-assigned U.S. Pat. No. 7,771,425 entitled "Vessel Sealer And Divider Having A Variable Jaw Clamping Mechanism."

Handle assembly 30 includes a fixed handle 50 and a movable handle 40. Movable handle 40 of the handle assembly 30 is ultimately connected to a drive assembly (not shown). Applying force to move the movable handle 40 toward the fixed handle 50 pulls a drive sleeve or drive rod (not shown) proximally to impart movement to the jaw members 110 and 120 from an open position, wherein the jaw members 110 and 120 are disposed in spaced relation relative to one another, to a clamping or closed position, wherein the jaw members 110 and 120 cooperate to grasp tissue therebetween.

Forceps 10 includes an electrosurgical cable 15. Cable 15 may be formed from a suitable flexible, semi-rigid, or rigid cable, and may connect directly to a power generating source 28. Cable 15 may be internally divided into one or more cable leads each of which transmits energy through their respective feed paths to the end-effector assembly 100. Power generating source 28 may be any generator suitable for use with surgical devices, and may be configured to provide various frequencies of electromagnetic energy. Forceps 10 may alternatively be configured as a wireless device or battery-powered.

Figure 3:
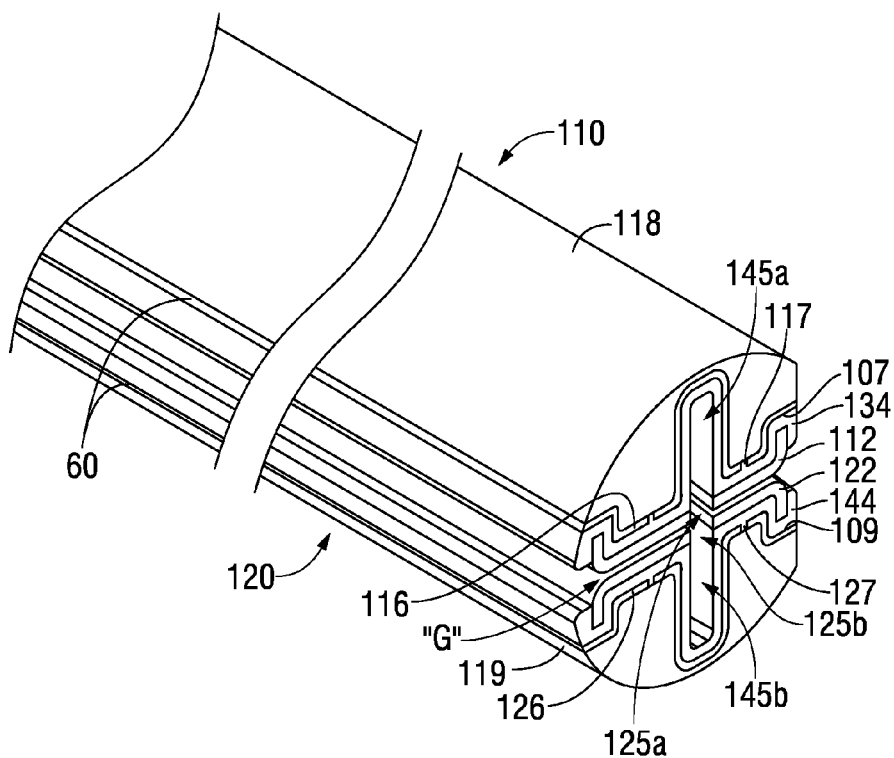
FIG. 3 is a perspective view of a cross-section of a matched pair of opposing jaw members in accordance with an embodiment of the present disclosure.

As shown in FIGS. 1 through 3, jaw members 110 and 120 include an electrically-conductive tissue-engaging surface or sealing plate 112 and 122, respectively, arranged in opposed relation relative to one another. Sealing plates 112 and 122 define longitudinally-extending elongated slots 125a and 125b, respectively. The shape and size of the sealing plates 112 and 122 may be varied from the configuration depicted in FIGS. 1 through 3.

Jaw member 120 includes a plurality of stop members 90 disposed on an inner-facing surface 123 of the sealing plate 122. Alternatively or in addition, one or more stop members 90 may be disposed on an inner-facing surface 113 of the sealing plate 112. Stop members 90 may be configured to facilitate and/or enhance the gripping and manipulation of tissue and/or configured to define the gap distance "G" (FIG. 3) between the opposing jaw members 110 and 120 during the sealing of tissue. Stop members 90 may be disposed on or adjacent to one or both of the sealing plates 112 and 122, and/or operatively associated with one or both jaw members 110 and 120.

Jaw members 110 and 120, as shown in FIG. 2, include an outer housing 111 and 121, respectively. Outer housings 111 and 121 may define a cavity (not shown) therein configured to at least partially encapsulate and/or securely engage the sealing plates 112 and 122, respectively, and/or other jaw member components. In some embodiments, the outer housings 111 and 121 may be made from an electrically and thermally insulating material, e.g., a temperature resistant plastic or a ceramic.

Jaw members 110 and 120, as shown in FIG. 3, include a support structure 118 and 119, respectively, and an insulator member 134 and 144, respectively. Support structures 118 and 119 may be formed from any suitable material or combination of materials, e.g., metallic material, plastic and the like, and may be formed by any suitable process, e.g., machining, stamping, electrical discharge machining (EDM), forging, casting, injection molding, metal injection molding (MIM), and/or fineblanking. Examples of metallic material that may be suitable include aluminum and alloys thereof, plated brass, stainless steel, stainless steel alloys, beryllium copper, etc.

Insulator members 134 and 144 are disposed between the support structures 118 and 119 and the sealing plates 112 and 122, respectively. Insulator members 134 and 144 generally include outer surfaces 107 and 109, respectively. Insulator members 134 are configured to define knife channels 145a and 145b, respectively.

In some embodiments, the insulator members 134 and 144 include one or more boss members 117 and 127, respectively, protruding from the outer surfaces 107 and 109 thereof, e.g., disposed on opposite sides of the knife channels 145a and 145b, respectively. In some embodiments, as shown for example in FIG. 9, the boss members 117 and 127 may be configured as single unitary structures. Alternatively, the boss members 117 and 127 may be configured as a plurality of separate, spaced-apart structures of any suitable configuration, e.g., a plurality of a regular or irregular geometric shape. The boss members 117 and 127 help to define bonding regions 116 and 126, respectively, disposed between the insulator members 134 and 144 and the support structures 118 and 119, respectively. As described later in this description, a bonding material, e.g., a high-temperature epoxy adhesive, is disposed in the bonding regions 116 and 126.

FIGS. 4 through 7 show embodiments of an alignment spacer for use in connection with the manufacture of a matched pair of jaw members 110 and 120. Alignment spacer embodiments as described herein are configured for use to align the sealing plates 112 and 122 in relation with one another. In some embodiments, the presently-disclosed alignment spacer is configured to facilitate aligning the slot 125a and the knife channel 145a of the first jaw member 110 and the slot 125b and the knife channel 145b of the second jaw member 120 in a direction along the longitudinal axis "A-A" of the end-effector assembly 100 and in a direction substantially transverse to the longitudinal axis "A-A".

Figure 4:
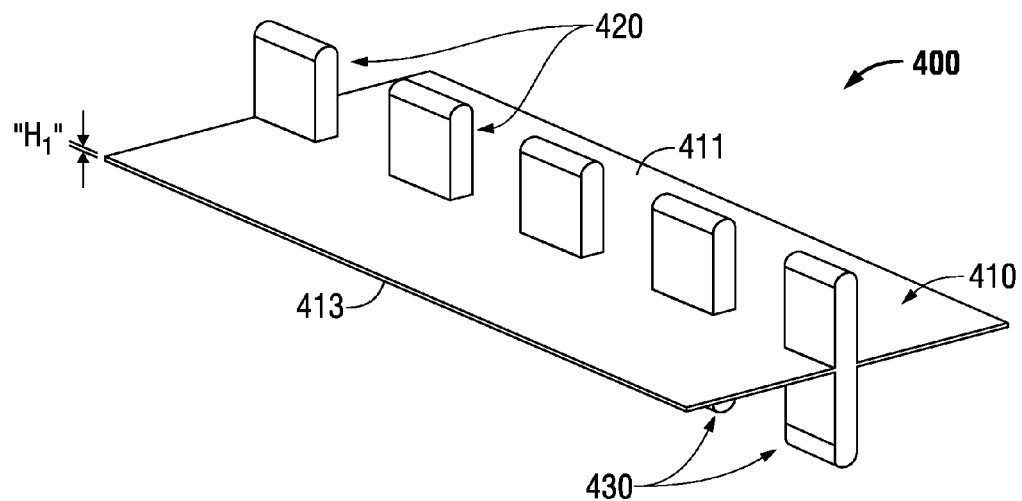
FIG. 4 is a perspective view of an alignment spacer for use in connection with the manufacture of a matched pair of opposing jaw members in accordance with an embodiment of the present disclosure.

FIG. 4 shows an alignment spacer 400 for use in connection with the manufacture of the matched pair of jaw members 110 and 120. Alignment spacer 400 is configured to set the jaw gap (e.g., gap "G" disposed between the inner-facing surfaces of the jaw members 110 and 120 shown in FIGS. 3 and 14) and also configured to align the sealing plates 112 and 122 in relation to one another. Alignment spacer 400 may be formed from any suitable material or combination of materials, e.g., plastic, and may be formed by any suitable process, e.g., injection molding.

Alignment spacer 400 generally includes a substrate 410 having a first surface 411 and a second surface 413. In some embodiments, the substrate 410 may have a generally rectangular shape. Although the substrate 410 depicted in FIG. 4 includes straight edges, other shapes including curves may be utilized. Substrate 410 may have any suitable height "$H_1$". As shown in FIG. 4, the alignment spacer 400 includes a plurality of alignment members 420 associated with the first surface 411 of the substrate 410, and a plurality of alignment members 430 associated with the second surface 413. Alignment members 420 and 430 may be configured to engage the knife channels 145a and 145b, respectively.

Figure 5:
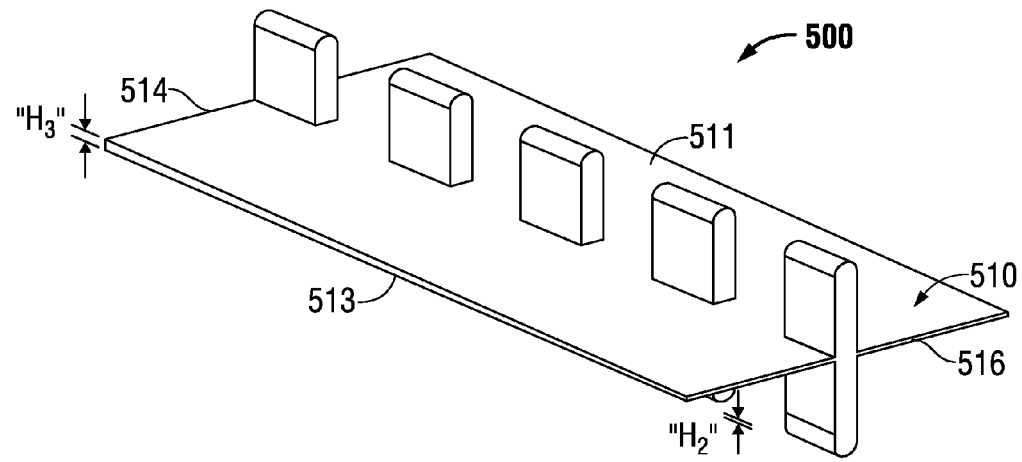
FIG. 5 is a perspective view of another embodiment of an alignment spacer for use in connection with the manufacture of a matched pair of opposing jaw members in accordance with the present disclosure.

FIG. 5 shows an alignment spacer 500 for use in connection with the manufacture of a matched pair of opposing jaw members in accordance with the present disclosure. Alignment spacer 500 is configured to set the tip bias of the jaw members 110 and 120 and also configured to align the sealing plates 112 and 122 in relation to one another. Alignment spacer 500 includes a substrate 510 having a first surface 511 and a second surface 513. As shown in FIG. 5, the substrate 510 has a first height "$H_2$" at its distal end 516 and a second height "$H_3$" at its proximal end 514, resulting in a wedge-like shape, e.g., configured to set the tip bias of the jaw members 110 and 120.

Figure 6:
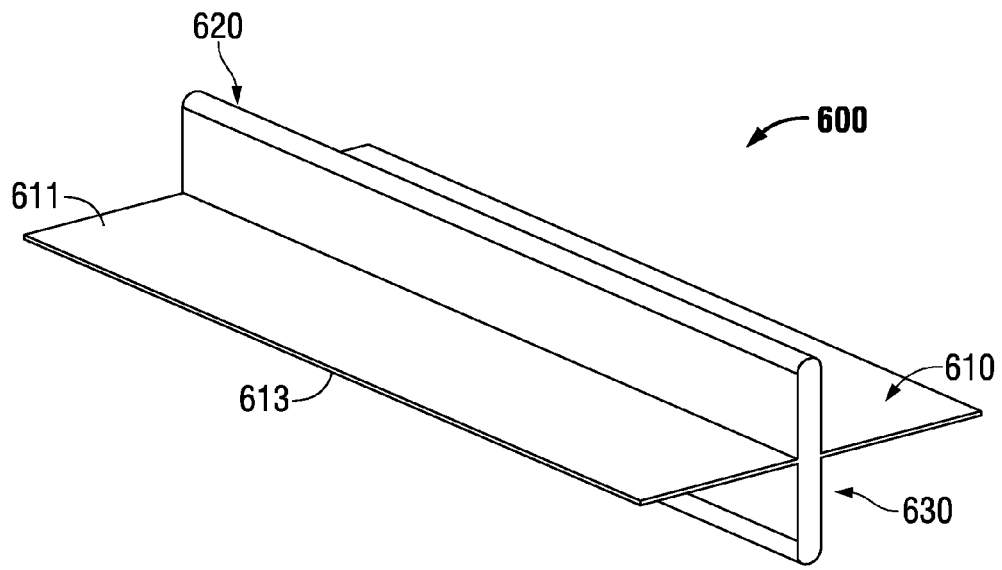
FIG. 6 is a perspective view of yet another embodiment of an alignment spacer for use in connection with the manufacture of a matched pair of opposing jaw members in accordance with the present disclosure.

FIG. 6 shows an alignment spacer 600 for use in connection with the manufacture of a matched pair of opposing jaw members in accordance with the present disclosure and includes a substrate 610 having a first surface 611 and a second surface 613. Alignment spacer 600 is configured to set the jaw gap (e.g., gap "G" shown in FIGS. 3 and 14) and also configured to align the sealing plates 112 and 122 in relation to one another. Substrate 610 shown in FIG. 6 is similar to the substrate 410 of FIG. 4, and further description thereof is omitted in the interests of brevity.

As shown in FIG. 6, a unitary alignment member 620 is associated with the first surface 611 of the substrate 610, and a unitary alignment member 630 is associated with the second surface 613 of the substrate 610. This configuration may enhance the rigidity and/or durability of the alignment spacer 600. As shown in FIG. 6, the unitary alignment members 620 and 630 have an elongated bar-like shape, which may increase ease of manufacture and/or inspection, and which may improve usability, e.g., depending on the configuration of the knife channels 145a and 145b.

Figure 7:
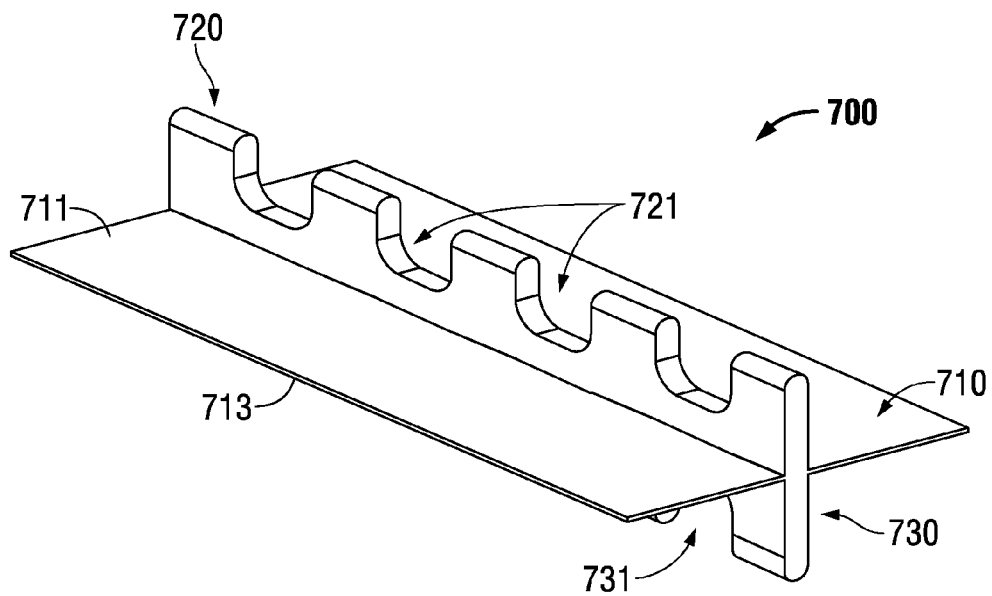
FIG. 7 is a perspective view of still another embodiment of an alignment spacer for use in connection with the manufacture of a matched pair of opposing jaw members in accordance with the present disclosure.

In FIG. 7, an alignment spacer 700 for use in connection with the manufacture of a matched pair of opposing jaw members in accordance with the present disclosure is shown and includes a substrate 710. As shown in FIG. 7, an alignment member 720 is associated with a first surface 711 of the substrate 710, and an alignment member 730 is associated with a second surface 713 of the substrate 710. Substrate 710 is similar to the substrate 410 shown in FIG. 4, and further description thereof is omitted in the interests of brevity. Alignment members 720 and 730 shown in FIG. 7 are similar to the elongated bar-like shaped alignment members 620 and 630 of FIG. 7, except for the curved, cutout portions 721 and 731.

Figure 8A:
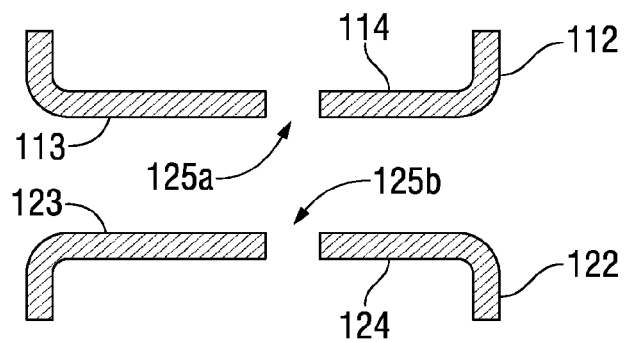
FIGS. 8A through 8E show a schematic representation of a sequence of operations of a method of manufacturing a matched pair of opposing jaw members in accordance with an embodiment of the present disclosure.
Figure 8B:
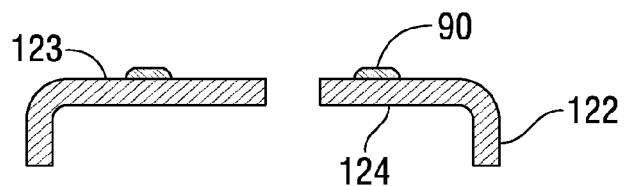
Figure 8C:
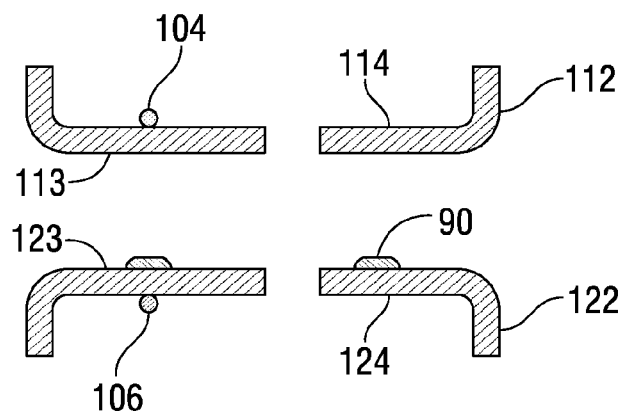
Figure 8D:
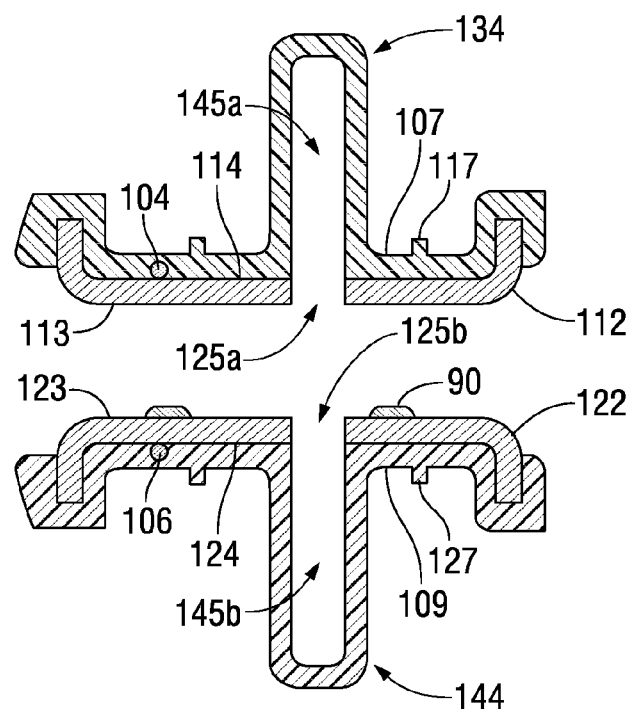
Figure 8E:
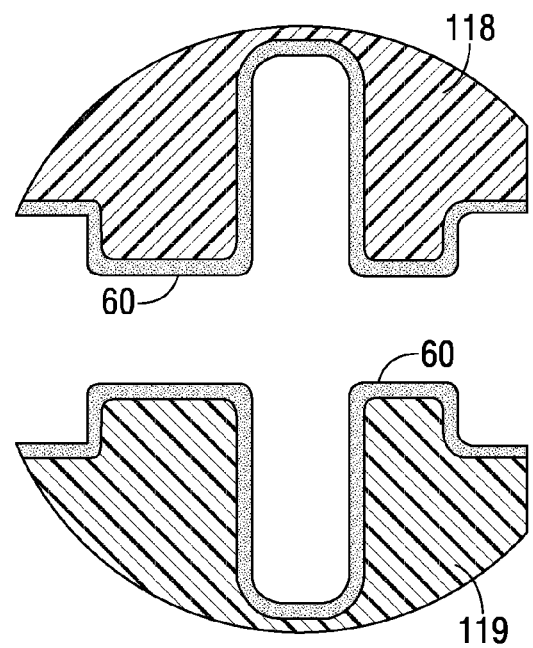

FIGS. 8A through 8E schematically illustrates a series of operations according to a method of manufacturing a matched pair of opposing jaw members. One or more of the operations depicted in the illustrative embodiment of FIGS. 8A through 8E may be performed in combination and in a different order than presented herein without departing from the scope of the disclosure. The operations, which are described in more detail below, generally involve the depositing of a plurality of stop members 90 onto the sealing plate 122 (FIG. 8B), the coupling of electrical leads 104 and 106 to the sealing plates 112 and 122, respectively (FIG. 8C), the coupling of the insulator members 134 and 144 to the sealing plates 112 and 122, respectively (FIG. 8D), and the placing of a bonding material 60 onto one or more surfaces of the inner side of the support structures 118 and 119 (FIG. 8E).

Sealing plates 112 and 122, as shown in FIGS. 8A through 8C, have an inner-facing surface 113 and 123, respectively, and an outer surface 114 and 124, respectively. Sealing plates 112 and 122 may be formed from any suitable material or combination of materials, e.g., metallic material, and may be formed by any suitable process, e.g., machining, stamping, metal injection molding (MIM), and/or fineblanking. The shape and size of the sealing plates 112 and 122 may be varied from the configuration depicted in FIGS. 8A through 8C.

A plurality of stop members 90, as shown in FIG. 8B, is deposited onto the inner-facing surface 123 of the sealing plate 122. One or more stop members 90 may be deposited onto either one or both of the sealing plates 112 and 122. In some embodiments, a plurality of stop members 90 may be deposited onto one of the sealing plates (e.g., sealing plate 122) prior to the coupling of the insulator members 134 and 144 to the sealing plates 112 and 122, respectively. Stop members 90 may be made from any suitable insulative material, e.g., peek, nylon and/or ceramic. Examples of stop member embodiments as well as various manufacturing and assembling processes for attaching and/or affixing the stop members 90 to the sealing plates 112 and 122 are described in commonly-assigned International Publication No. WO 2002/080796 filed on Apr. 6, 2001, entitled "Vessel Sealer And Divider With Non-Conductive Stop Members."

Electrical leads 104 and 106, as shown in FIG. 8C, are coupled to the outer surfaces 114 and 124 of the sealing plates 112 and 122, respectively. Electrical leads 104 and 106 may be electrically-coupled to the sealing plates 112 and 122 by any suitable manner of electrical connection, e.g., soldering, welding, or laser welding. One or more electrical leads may be electrically-coupled by any suitable manner to either one or both of the sealing plates 112 and 122.

Insulator members 134 and 144, as shown in FIG. 8D, may include any of a variety of suitable non-electrically conductive materials such as polymeric materials, e.g., plastics, and/or other insulative materials, and may be formed by any suitable process. Longitudinally-extending knife channels 145a and 145b defined by the insulator members 134 and 144, respectively, may be configured to align with the longitudinally-extending slots 125a and 125b defined by the sealing plates 112 and 122, respectively, to permit longitudinal reciprocation of a knife blade (not shown).

Insulator members 134 and 144 may be coupled to one or more surfaces of the sealing plates 112 and 122, respectively, by any suitable process. In some embodiments, the insulator members 134 and 144 are overmolded onto the sealing plates 112 and 122, respectively. Alternatively, the insulator members 134 and 144 may be formed by injection molding, and may be adhesively-attached to the sealing plates 112 and 122, respectively. A variety of different configurations of stop members 90 may be deposited onto either one or both of the sealing plates 112 and 122, e.g., prior to and/or after the coupling of the insulator members 134 and 144 to the sealing plates 112 and 122, respectively. In some embodiments, as shown for example in FIG. 8D, the insulator members 134 and 144 include one or more boss members 117 and 127, respectively, protruding from the outer surfaces 107 and 109, respectively. The boss members 117 and 127 help to define bonding regions 116 and 126, respectively, disposed between the insulator members 134 and 144 and the support structures 118 and 119, respectively.

Figure 9:
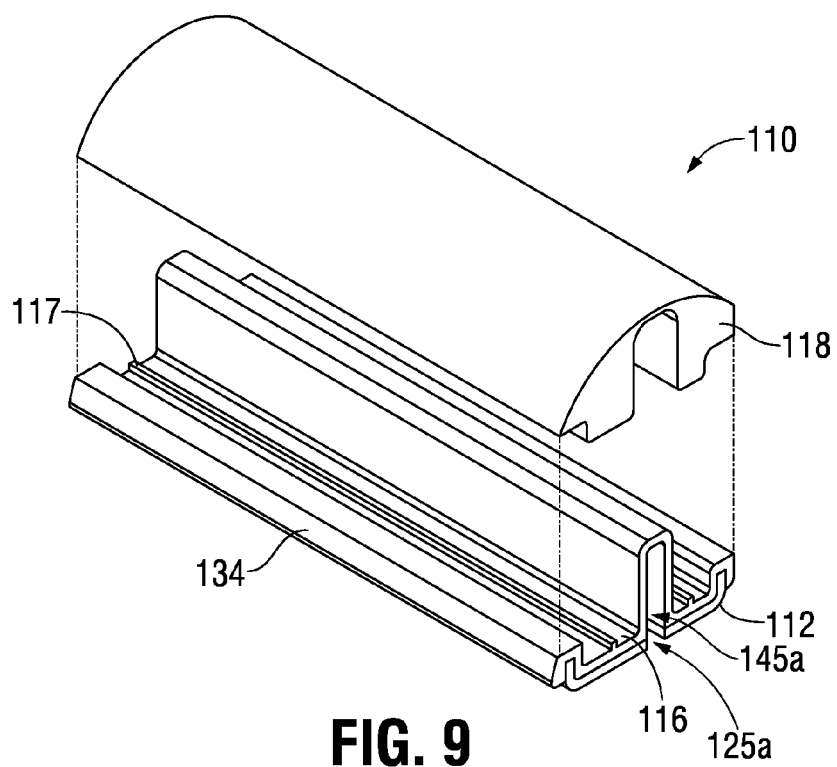
FIGS. 9 and 10 are perspective views of portions of opposing jaw members, with parts separated, in accordance with an embodiment of the present disclosure.
Figure 10:
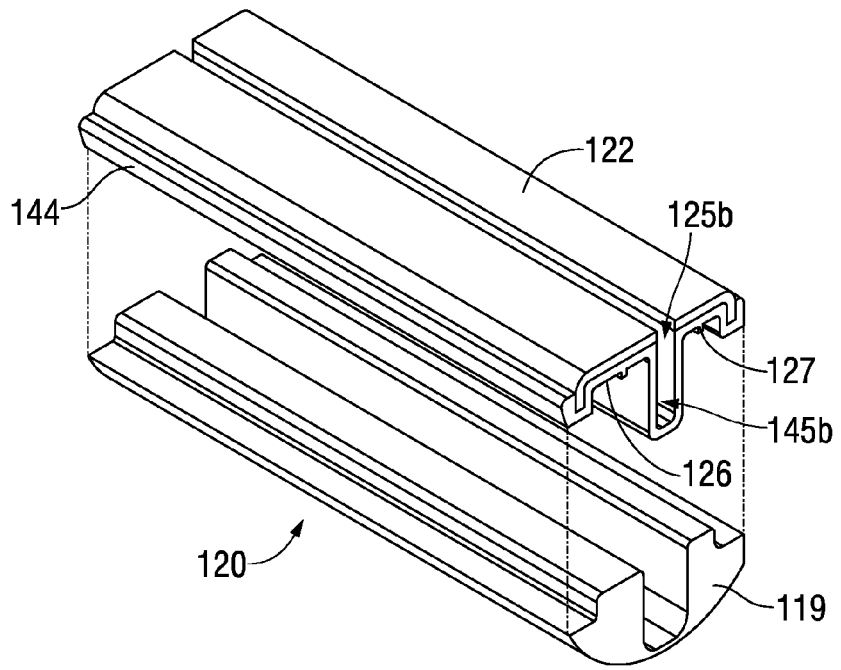

FIGS. 9 and 10 show the support structures 118 and 119 disposed in spaced relation to the insulator members 134 and 144, respectively, and in an aligned configuration relative to one another. In some embodiments, a bonding material 60 may be placed within the bonding regions 116 and 126 prior to the positioning of the support structures 118 and 119 into mating engagement with the insulator members 134 and 144, respectively. In some embodiments, the bonding material 60 may be placed on one or more inner-facing surfaces of the support structures 118 and 119 as shown in FIG. 8E. It is to be understood that the bonding material 60 may be deposited onto one or more surfaces of the support structures 118 and 119 and/or one or more surfaces of the insulator members 134 and 144. In at least one alternative embodiment, the bonding material 60 may be placed (e.g., by injection) into the bonding regions 116 and 126 after the positioning of the support structures 118 and 119 into mating engagement with the insulator members 134 and 144, respectively.

Figure 11:
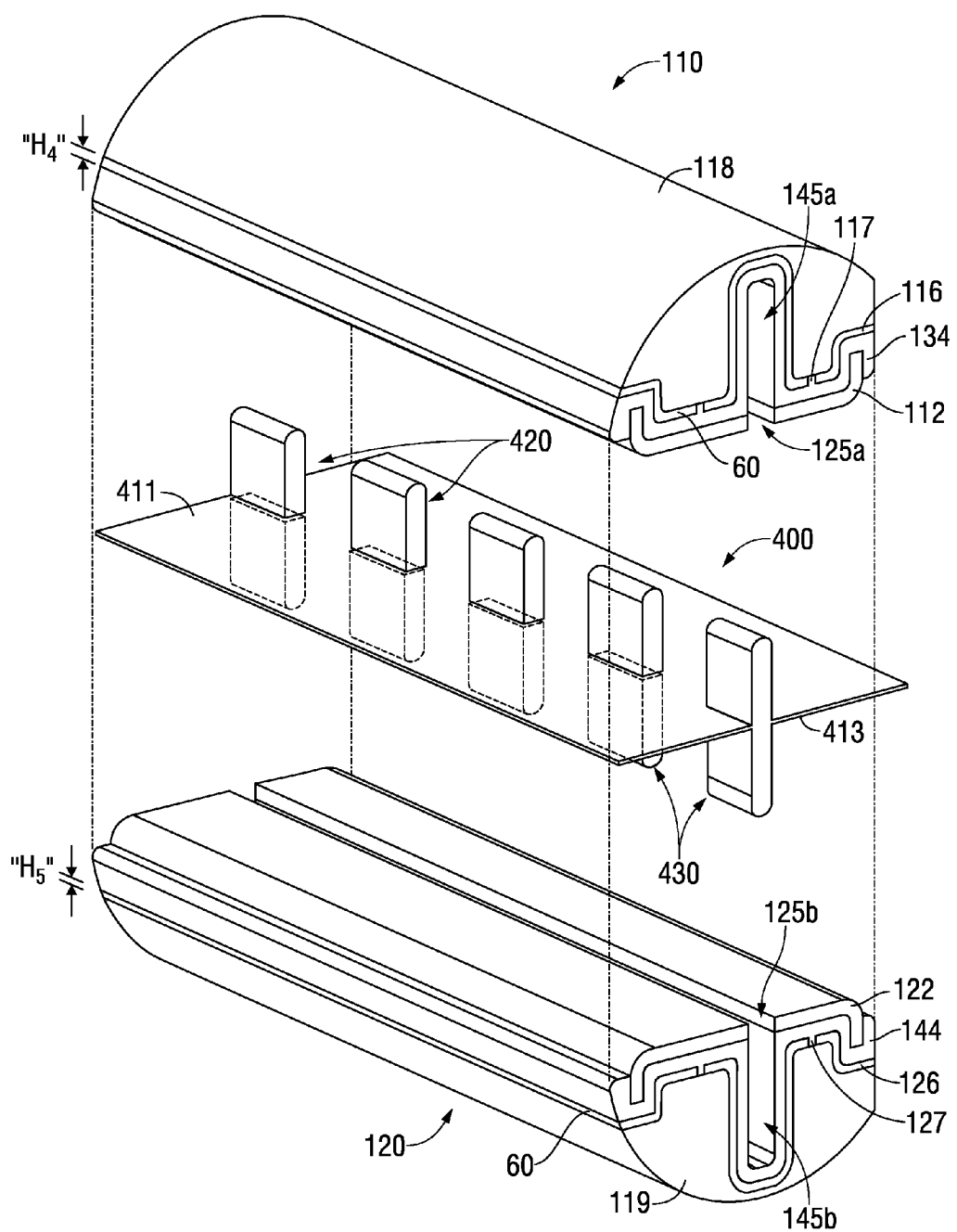
FIG. 11 is a perspective view of the matched pair of opposing jaw members of FIG. 3, shown with the alignment spacer of FIG. 4 disposed in spaced relation therebetween, in accordance with an embodiment of the present disclosure.

FIG. 11 shows the opposing jaw members 110 and 120 with the alignment spacer 400 disposed in spaced relation therebetween. As shown FIG. 11, the plurality of alignment members 420 protruding from the first surface 411 of the substrate 410 of the alignment spacer 400 are configured to engage with the knife channel 145a of the jaw member 110, and the alignment members 430 protruding from the second surface 413 of the substrate 410 are configured to engage with the knife channel 145b of the jaw member 120. When the opposing jaw members 110 and 120 are brought into a clamped engagement with the alignment spacer 400, as shown for example in FIG. 13, the jaw members 110 and 120 may be coupled to one another in any suitable manner. In some embodiments, the jaw members 110 and 120 may be pivotably mounted with respect to one another, e.g., mounted about a pivot pin 103 (FIGS. 1 and 2).

Figure 12:
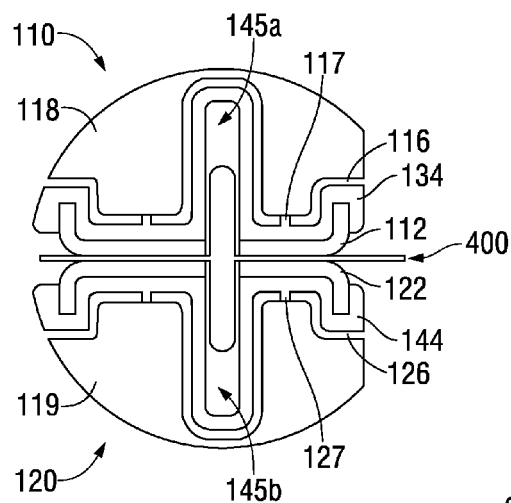
FIG. 12 is a cross-sectional view of a matched pair of opposing jaw members disposed in a clamped engagement with the alignment spacer of FIG. 4 in accordance with an embodiment of the present disclosure.

In some embodiments, as shown in FIG. 12, the support structures 118 and 119 may be positioned into mating engagement with the insulator members 134 and 144, respectively, prior to the depositing of the bonding material 60 within the bonding regions 116 and 126. A holding fixture (not shown) may be provided for retaining the support structures 118 and 119 in mating engagement with the insulator members 134 and 144, respectively, e.g., during the placing of the bonding material 60 into the bonding regions 116 and 126 and/or the curing of the bonding material 60, and/or to facilitate other operations, e.g., the coupling of the first jaw member 110 to the second jaw member 120.

Figure 13:
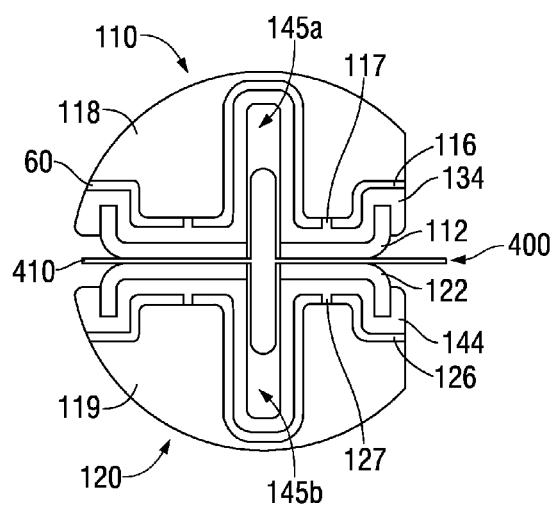
FIG. 13 is a cross-sectional view of the matched pair of opposing jaw members of FIG. 12 shown with a bonding material disposed in bonding regions in accordance with an embodiment of the present disclosure.

FIG. 13 shows the support structures 118 and 119 disposed in mating engagement with the insulator members 134 and 144, respectively, with the bonding material 60 disposed within the bonding regions 116 and 126, and the sealing plates 112 and 122 disposed in a clamped engagement with the alignment spacer 400. After the opposing jaw members 110 and 120 are coupled to one another, and after curing of the bonding material 60, the alignment spacer 400 may be released and removed from the jaw members 110 and 120.

In some embodiments, the support structures 118 and 119, the insulator members 134 and 144, and/or the sealing plates 112 and 122 may be at least partially encapsulated by outer insulative housings (e.g., outer housing 111 and 121 shown in FIG. 2) by way of a subsequent overmolding process.

Figure 14:
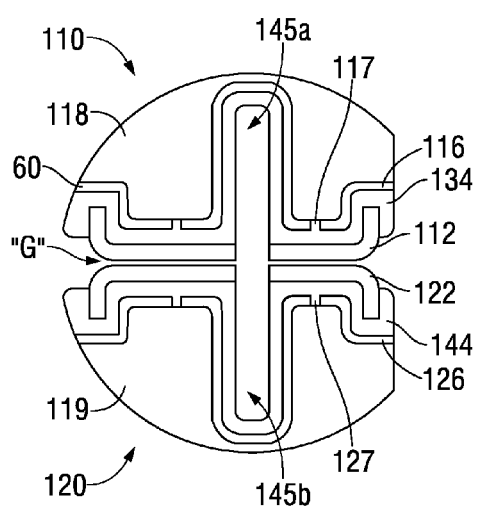
FIG. 14 is a cross-sectional view of the matched pair of opposing jaw members of FIG. 13, shown without the alignment spacer, in accordance with an embodiment of the present disclosure.

In FIG. 14, the matched pair of opposing jaw members 110 and 120, assembled in accordance with the presently-disclosed methods of manufacturing a matched pair of opposing jaw members, is shown without the alignment spacer 400 of FIG. 14.

In accordance with an embodiment of the present disclosure, a method of manufacturing a matched pair of opposing jaw members 110 and 120 of an end-effector assembly 100 includes: assembling a first jaw member 110 having a knife channel 125a, 145a; assembling a second jaw member 120 having a knife channel 145b; and setting a jaw gap "G" and aligning a sealing plate 112 of the first jaw member 110 and a sealing plate 122 of the second jaw member 120 in relation to one another by bringing the first jaw member 110 and the second jaw member 120 into clamped engagement with an alignment spacer 400. The alignment spacer 400 is configured to engage the knife channel 145a of the first jaw member 110 and the knife channel 145b of the second jaw member 120. The method also includes coupling the first jaw member 110 to the second jaw member 120.

In some embodiments of the above-described method of manufacturing a matched pair of opposing jaw members 110 and 120, aligning the sealing plates 112 and 122 in relation to one another includes aligning the knife channel 145a of the first jaw member 110 and the knife channel 145b of the second jaw member 120 in a direction along the longitudinal axis "A-A" of the end-effector assembly 100 and in a direction substantially transverse to the longitudinal axis "A-A".

In some embodiments, assembling the first jaw member 110 includes electrically-coupling an electrical lead 104 to the first sealing plate 112 and overmolding a first insulator member 134 onto the first sealing plate 112. In some embodiments, assembling the first jaw member 110 may further include coupling a first support structure 118 to the first insulator member 134. In some embodiments, coupling the first support structure 118 to the first insulator member 134 includes depositing a bonding material 60 within a bonding region 116 disposed between the first insulator member 134 and the first support structure 118.

In some embodiments, one or more boss members 117 associated with the first insulator member 134 and/or one or one or more boss members 127 associated with the second insulator member 144 may be configured to be crushable or collapsible or otherwise deformable to allow the alignment spacer 400 to set the jaw gap (e.g., gap "G" disposed between the inner-facing surfaces of the jaw members 110 and 120 shown in FIGS. 3 and 14). In turn, the height "$H_4$" of the bonding region 116 may vary depending on the deformation of one or more boss members 117, and/or the height "$H_5$" (FIG. 11) of the bonding region 126 may vary depending on the deformation of one or more boss members 127.

In accordance with an embodiment of the present disclosure, a method of manufacturing a matched pair of opposing jaw members 110 and 120 of an end-effector assembly 100 includes assembling a first jaw member 110, including coupling an electrical lead 104 to a first sealing plate 112, coupling (e.g., overmolding) a first insulator member 134 onto the first sealing plate 112, and coupling a first support structure 118 to the first insulator member 134. The method includes assembling a second jaw member 120, including coupling (e.g., overmolding) a second insulator member 144 onto a second sealing plate 122, and coupling a second support structure 119 to the second insulator member 144. The method also includes setting a jaw gap "G" and aligning the first sealing plate 112 and the second sealing plate 122 in relation to one another by bringing the first jaw member 110 and the second jaw member 120 into clamped engagement with an alignment spacer 400, and movably coupling the first jaw member 110 to the second jaw member 120 while in clamped engagement with the alignment spacer 400. The alignment spacer 400 is configured to engage a first knife channel 145a defined by the first insulator member 134 and a second knife channel 145b defined by the second insulator member 144.

In accordance with embodiments of the above-described methods of manufacturing a matched pair of opposing jaw members 110 and 120, aligning the first sealing plate 112 and the second sealing plate 122 in relation to one another includes aligning an elongated slot 125a of the first sealing plate 112 and an elongated slot 125b of the second sealing plate 122 in a direction along a longitudinal axis "A-A" of the end-effector assembly 100 and in a direction substantially transverse to the longitudinal axis "A-A". In some embodiments, bringing the first jaw member 110 and the second jaw member 120 into clamped engagement with the alignment spacer 400 aligns the slot 125a and the knife channel 145a of the first jaw member 110 and the slot 125b and the knife channel 145b of the second jaw member 120 in a direction along the longitudinal axis "A-A" of the end-effector assembly 100 and in a direction substantially transverse to the longitudinal axis "A-A".

In accordance with any one of the above-described methods of manufacturing a matched pair of opposing jaw members 110 and 120 of an end-effector assembly 100, a bonding material 60 may be placed on the first support structure 118 and/or the second support structure 119. In some embodiments, a bonding material 60 may be placed on a support structure (e.g., first support structure 118) and the support structure coupled to an insulator member (e.g., first insulator member 134), after which the alignment spacer 400 may be added with the other jaw member (e.g., second jaw member 120). In accordance with any one of the above-described methods, the matched pair of opposing jaw members 110 and 120 may be pivotably mounted about a pin configured to permanently join the jaw members. In accordance with any one of the above-described methods, the matched pair of opposing jaw members 110 and 120 may be welded together.

The above-described methods of manufacturing a pair of opposing jaw members of an end-effector assembly may also include releasing the alignment spacer 400 from a matched pair of opposing jaw members 110 and 120, e.g., after releasing the matched pair of opposing jaw members 110 and 120 from a holding fixture. In accordance with any one of the above-described methods, the alignment spacer 400 may be released and removed at any suitable point.

The above-described methods of manufacturing a pair of opposing jaw members may utilize sealing plates and/or support structures fabricated with low manufacturing tolerances, thereby reducing costs, wherein jaw gap, tip bias, and seal-plate alignment may be set by the use of an alignment spacer in conjunction with the use of one or more (deformable) boss members associated with the first insulator member and/or one or more (deformable) boss members associated with the second insulator member.

The above-described end-effector assembly embodiments including any combination of features of the above-described matched pair of opposing jaw members may utilize jaw member components of varied geometries, e.g., lengths and curvatures, such that variously-configured matched pairs of opposing jaw members may be fabricated and assembled into various end-effector configurations, e.g., depending upon design of specialized surgical instruments.

The above-described surgical instrument embodiments may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Although embodiments have been described in detail with reference to the accompanying drawings for the purpose of illustration and description, it is to be understood that the disclosed processes and apparatus are not to be construed as limited thereby. It will be apparent to those of ordinary skill in the art that various modifications to the foregoing embodiments may be made without departing from the scope of the disclosure.

What is claimed is:

1. A method of manufacturing a pair of opposing jaw members of an end-effector assembly, comprising:
   assembling a first jaw member having a knife channel,
   assembling a second jaw member having a knife channel,
   setting a jaw gap and aligning a first sealing plate of the first jaw member and a second sealing plate of the second jaw member in relation to one another by bringing the first jaw member and the second jaw member into clamped engagement with an alignment spacer, the alignment spacer configured to engage the knife channel of the first jaw member and the knife channel of the second jaw member; and
   coupling the first jaw member to the second jaw member.

2. The method of claim 1, wherein aligning the first sealing plate of the first jaw member and the second sealing plate of the second jaw member in relation to one another includes aligning a first elongated slot defined by the first sealing plate and a second elongated slot defined by the second sealing plate in a direction along a longitudinal axis of the end-effector assembly.

3. The method of claim 1, wherein bringing the first jaw member and the second jaw member into clamped engagement with the alignment spacer aligns the knife channel of the first jaw member and the knife channel of the second jaw member in a direction along a longitudinal axis of the end-effector assembly and in a direction substantially transverse to the longitudinal axis.

4. The method of claim 1, wherein bringing the first jaw member and the second jaw member into clamped engagement with the alignment spacer sets a tip bias of the first jaw member and the second jaw member.

5. The method of claim 1, wherein assembling the first jaw member includes electrically-coupling an electrical lead to the first sealing plate.

6. The method of claim 5, wherein assembling the first jaw member further includes coupling a first insulator member to the first sealing plate.

7. The method of claim 6, wherein coupling the first insulator member to the first sealing plate includes overmolding the first insulator member onto the first sealing plate.

8. The method of claim 7, wherein assembling the first jaw member further includes coupling a first support structure to the first insulator member.

9. The method of claim 8, wherein coupling the first support structure to the first insulator member includes depositing a bonding material within a bonding region disposed between the first insulator member and the first support structure.

10. The method of claim 1, wherein assembling the second jaw member includes overmolding a second insulator member onto the second sealing plate.

11. The method of claim 1, further comprising releasing the alignment spacer from the pair of opposing jaw members after coupling the first jaw member to the second jaw member.

12. A method of manufacturing a pair of opposing jaw members of an end-effector assembly, comprising:
  assembling a first jaw member, including: coupling an electrical lead to a first sealing plate; coupling a first insulator member to the first sealing plate; and coupling a first support structure to the first insulator member;
  assembling a second jaw member, including: coupling a second insulator member to a second sealing plate; and coupling a second support structure to the second insulator member;
  setting a jaw gap and aligning the first sealing plate and the second sealing plate in relation to one another by bringing the first jaw member and the second jaw member into a clamped engagement with an alignment spacer configured to engage a first knife channel defined by the first insulator member and a second knife channel defined by the second insulator member; and
  movably coupling the first jaw member to the second jaw member while in clamped engagement with the alignment spacer.

13. The method of claim 12, wherein aligning the first sealing plate and the second sealing plate in relation to one another aligns a first elongated slot defined by the first sealing plate and a second elongated slot defined by the second sealing plate in a direction along a longitudinal axis of the end-effector assembly.

14. The method of claim 12, wherein bringing the first jaw member and the second jaw member into clamped engagement with the alignment spacer aligns the first knife channel defined by the first insulator member and the second knife channel defined by the second insulator member in a direction along a longitudinal axis of the end-effector assembly and in a direction substantially transverse to the longitudinal axis.

15. The method of claim 12, wherein coupling the first support structure to the first insulator member includes depositing a bonding material within a bonding region disposed between the first insulator member and the first support structure.

16. The method of claim 15, wherein depositing the bonding material within the bonding region includes placing the bonding material by injection into the bonding region after positioning of the first support structure into mating engagement with the first insulator member.

17. The method of claim 15, wherein depositing the bonding material within the bonding region includes placing the bonding material prior to positioning of the first support structure into mating engagement with the first insulator member.

18. The method of claim 17, wherein placing the bonding material prior to positioning of the first support structure into mating engagement with the first insulator member includes placing the bonding material on at least one surface of an inner side of the first support structure.

19. The method of claim 18, further comprising releasing the alignment spacer from the pair of opposing jaw members after curing of the bonding material.

* * * * *